US010782293B2

(12) United States Patent
Baird et al.

(10) Patent No.: US 10,782,293 B2
(45) Date of Patent: Sep. 22, 2020

(54) COMPOSITIONS AND METHODS

(71) Applicant: DIAGNOSTIG LTD, Bangor Gwynedd (GB)

(72) Inventors: Mark Stephen Baird, Bangor Gwynedd (GB); Christopher David Gwenin, Bangor Gwynedd (GB); Juma'a Raheem Najeem Al Dulayymi, Bangor Gwynedd (GB); Salam Ghafour Taher, Bangor Gwynedd (GB)

(73) Assignee: DIAGNOSTIG LTD, Bangor (GB)

( * ) Notice: Subject to any disclaimer, the term of this patent is extended or adjusted under 35 U.S.C. 154(b) by 132 days.

(21) Appl. No.: 15/752,041

(22) PCT Filed: Aug. 12, 2016

(86) PCT No.: PCT/GB2016/052509

§ 371 (c)(1),
(2) Date: Feb. 12, 2018

(87) PCT Pub. No.: WO2017/025758

PCT Pub. Date: Feb. 16, 2017

(65) Prior Publication Data

US 2019/0250160 A1 Aug. 15, 2019

(30) Foreign Application Priority Data

Aug. 13, 2015 (GB) .................................. 1514415.7

(51) Int. Cl.

| | |
|---|---|
| ***A61K 39/00*** | (2006.01) |
| ***A61K 39/02*** | (2006.01) |
| ***A61K 39/04*** | (2006.01) |
| ***G01N 33/569*** | (2006.01) |
| ***C07H 13/04*** | (2006.01) |
| ***C07K 14/36*** | (2006.01) |
| *A61K 47/26* | (2006.01) |

(52) U.S. Cl.
CPC ....... *G01N 33/56933* (2013.01); *C07H 13/04* (2013.01); *C07K 14/36* (2013.01); *A61K 47/26* (2013.01); *G01N 2333/30* (2013.01); *G01N 2469/20* (2013.01)

(58) Field of Classification Search
CPC ......... A61K 39/00; A61K 39/02; A61K 39/04
USPC ......................... 424/234.1, 248.1; 435/4, 7.1
See application file for complete search history.

(56) References Cited

FOREIGN PATENT DOCUMENTS

| | | | |
|---|---|---|---|
| JP | 57098218 | | 6/1982 |
| JP | 2004003912 | | 1/2004 |
| JP | 2006312604 | | 11/2006 |
| WO | 2012131394 | A1 | 10/2012 |
| WO | 2013186679 | A1 | 12/2013 |
| WO | 2014184768 | A1 | 11/2014 |
| WO | 2016024116 | A1 | 2/2016 |
| WO | 2016024118 | A1 | 2/2016 |

OTHER PUBLICATIONS

Laneele, M.A., et al. European AJournal of Biochemistry, vol. 12, No. 2, pp. 296-300, 1970.*
Laneelle, M.A., et al., European AJournal of Biochemistry, vol. 177, No. 3, pp. 631-635, 1988.*
Al Dulayymi et al., "The synthesis of single enantiomers of meromycolic acids from mycobacterial wax esters", Tetrahedron 62 (2006) pp. 11867-11880.
Laneelle et al., "Structure d'acides mycoliques et d'un intermediaire dans la biosynthese d'acides mycoliques dicarboxyliques", Eur. J. Biochem. 12, (1970) pp. 296-300 (English Abstract Provided).
Laneele et al., "Mycolic acids of *Mycobacterium aurum*: Structure and biogenetic implications", Eur. J. Biochem. 177, (1988) pp. 631-635.
Ndlandla et al., "Standardization of natural mycolic acid antigen composition and production for use in biomarker antibody detection to diagnose active tuberculosis", Journal of Immunological Methods 435 (2016) pp. 50-59.
Taher et al., "Synthesis of wax esters and related rehalose esters from *Mycobacterium avium* and other mycobacteria", Tetrahedron 72, (2016) pp. 3863-3876.
International Search Report for PCT Application No. PCT/GB2016/052509 dated Feb. 12, 2016, 5 pages.
Lumpkin, Henry Earle, "Installation of Mass Spectrometer 9 (MS-9) at Humble Oil and Refining Company," Henry Earle Lumpkin Photograph Collection, Box 1, 1963, 2 pages, Science History Institute, Philadelphia, available at https://digital.sciencehistory.org/works/zg64tk97v.
International Preliminary Report on Patentability issued in connection with International Application No. PCT/GB2016/052509 dated Feb. 13, 2018, 8 pages.

* cited by examiner

*Primary Examiner* — Rodney P Swartz
(74) *Attorney, Agent, or Firm* — Hoffman Warnick LLC

(57) ABSTRACT

A method of determining whether an individual is infected with a mycobacterial disease, the method comprising: (a) providing a system which comprises an antigen; (b) contacting the system with a sample obtained from the individual; and (c) detecting the presence or absence of binding of a biomarker in the sample with the antigen; wherein the antigen is a mycolic acid wax ester derived antigen.

12 Claims, No Drawings

COMPOSITIONS AND METHODS

The present invention relates to mycolic acid wax esters, to novel compounds of this type, to methods of preparing such compounds and uses and methods relating thereto. In particular the present invention relates to a method of detecting infection with mycobacteria and distinguishing between different mycobacterial infections.

The present invention is especially useful in the detection of Johne's disease in cattle. Johne's disease is caused by infection with *Mycobacterium avium* paratuberculosis and can be devastating to livestock populations. The control of the disease is challenging due to the lack of methods to quickly, cheaply and accurately diagnose the disease and the difficulty in distinguishing from infection with *Mycobacterium tuberculosis* and *Mycobacterium bovis* which causes bovine tuberculosis. There have been some studies suggesting that Crohn's disease in humans may be linked to ingestion of food infected with *M. avium.*

The present inventors have surprisingly found that using a single synthetic mycolic acid wax ester or a specific combination of such compounds as an antigen can help determine whether an individual is infected with Johne's disease. They have also prepared these antigens synthetically in high purity, improving the accuracy of the diagnosis.

According to a first aspect of the present invention, there is provided a method of determining whether an individual is infected with a mycobacterial disease, the method comprising:

(a) providing a system which comprises an antigen;
(b) contacting the system with a sample obtained from the individual; and
(c) detecting the presence or absence of binding of a biomarker in the sample with the antigen;

wherein the antigen is a mycolic acid wax ester derived antigen.

Suitably steps (a), (b) and (c) are carried out in the order (a) followed by (b) followed by (c).

The method may additionally or alternatively provide a method of determining whether an individual is infected with organisms, other than mycobacteria, which produce mycolic acid related molecules.

The antigen may be present on a substrate in the system and/or in one or more solutions or suspensions in the system. The antigen may be encapsulated in the system, for example in liposomes.

If further antigens are present in the system, the sample may be brought into contact with the antigens individually in order to allow the detection of the presence or absence of the binding of a biomarker in the sample with each antigen separately.

In some embodiments, the antigen is bound to a substrate in the system. Suitably the system comprises at least one substrate.

The system may comprise more than one substrate. If further antigens are present in the system, each of the antigens may be each bound to different substrates.

Suitably the first aspect of the present invention provides a method of determining whether an individual is infected with a mycobacterial disease, the method comprising:

(a) providing a substrate which carries an antigen;
(b) contacting the substrate with a sample obtained from the individual;
(c) detecting the presence or absence of binding of a biomarker in the sample with the antigen;

wherein the antigen is a mycolic acid wax ester derived antigen.

Suitably steps (a), (b) and (c) are carried out in the order (a) followed by (b) followed by (c).

The present invention provides a method of determining whether an individual is infected with a mycobacterial disease. The method involves detection of a biomarker in the sample that is indicative of infection with a mycobacterial disease. The biomarker is suitably an antibody.

The present invention preferably relates to a method of determining the presence or absence in a sample of an antibody indicative of infection with or exposure to mycobacteria.

Suitably the invention involves determining the presence or absence of a disease antibody indicative of infection with any disease caused by infection with mycobacteria. Examples of such diseases include tuberculosis, leprosy, pulmonary disease, burili ulcer and bovine tuberculosis and Johne's disease.

In some embodiments the method of the present invention is used to determine the presence or absence of an antibody indicative of infection with *Mycobacterium avium.*

There are two discrete species in the *Mycobacterium avium* complex (MAC):

*Mycobacterium avium* (*M. avium*).

*Mycobacterium intracellulare* (*M. intracellulare*).

These two species are difficult to differentiate and therefore they are also referred to collectively as *Mycobacterium avium-intracellulare* (MAI). Although it might more logically be termed the *Mycobacterium avium-intracellulare* complex such nomenclature has not been adopted. They are both opportunistic pathogens that affect the immunocompromised, particularly HIV-positive individuals. They can also affect immunocompetent people, especially those with pre-existing lung disease. MAC is ubiquitous. However, only a minority of people exposed to MAC will acquire infection.

*Mycobacterium avium* subspecies *paratuberculosis* (MAP) is an obligate pathogenic bacterium in the genus *Mycobacterium*. It is often abbreviated *M. paratuberculosis* or *M. avium* ssp. *paratuberculosis*. It is the causative agent of Johne's disease, which affects ruminants such as cattle, and also perhaps the human disease Crohn's disease.

Johne's disease is chronic inflammation of the intestine caused by *Mycobacterium avium* subspecies *paratuberculosis*. Infection and disease are mainly in domestic livestock but can affect many species including primates. Johne's is a new disease which emerged at the turn of the $19^{th}$ and $20^{th}$ centuries and principally involved Europe and North America. It has since spread to former low incidence regions to become a global problem. Crohn's disease is a chronic inflammation of the intestine in humans which emerged in Europe and North America mid $20^{th}$ century and increased to become a major healthcare problem. It has now spread to former low incidence regions. Infected animals shed *Mycobacterium avium* subspecies *paratuberculosis* in milk and into the environment. Human populations are widely exposed. Outcomes maybe influenced by microbial phenotype. Exposure to extracellular forms of these pathogens may confer some natural protection; exposure to intracellular forms which have passaged through milk macrophages or environmental protists may pose a greater threat to humans particularly individuals with an inherited or acquired susceptibility.

*M. avium* complex organisms will contain wax esters of mycolic acids, as will a number of other non-tuberculous mycobacteria.

Suitably the method of the present invention may be used to determine the presence or absence of an antibody indicative of infection with *Mycobacterium avium-intracellulare.*

In some preferred embodiments the method of the present invention is used to determine the presence or absence of an antibody indicative of infection with *Mycobacterium avium* paratuberculosis (Johne's disease).

The invention finds particular utility in determining the presence or absence in a sample of disease antibodies indicative of the presence of *Mycobacterium avium* paratuberculosis. The sample may be taken from any individual suspected of infection with *Mycobacterium avium* paratuberculosis. Suitably the individual is a ruminant, preferably a cow.

Step (a) of the method of the first aspect of the present invention may involve providing a substrate which carries the antigen.

The nature of the substrate will depend on the exact structure of the device. Suitable substrates are further described herein. For the avoidance of doubt the term substrate as used in relation to step (a) of the method of the first aspect refers to a carrier, for example a solid carrier, for the antigens. It is typically a plate or sheet-like material. In some embodiments the substrate is a gel.

The antigen is suitably immobilised on the substrate, for example on the surface of the substrate, for example as is further described herein.

Mycolic acids are long chain fatty acid compounds typically having 60 to 90 carbon atoms and are found as components of the cells of mycobacteria.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in FIG. I), can be differently substituted in both the proximal (the one nearer the hydroxy-acid) and the distal position (further from the carboxylic acid).

FIG. I

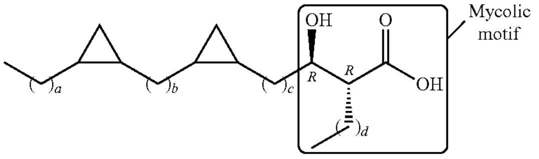

Meromycolate moiety
α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Mycolic acid wax esters are compounds having a similar structure to the above mycolic acids but including an ester functionality in the main chain. These compounds are found naturally in the bacterial cell walls of *Mycobacterium avium* and a range of other mycobacteria.

Suitably the mycolic acid wax esters derived antigen used in the method of the present invention comprises a compound of formula (I) or an ester or salt thereof:

(I)

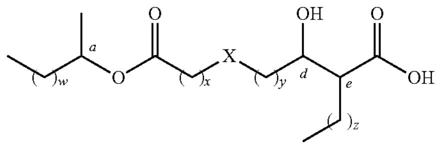

wherein w is from 2 to 40, x is from 2 to 40, y is from 2 to 40, z is from 4 to 40 and X is a three carbon fragment including an alkane, alkene or cyclopropyl moiety.

Suitably X is a group of formula (IIa), (IIb), (IIc) or (IId):

(IIa)

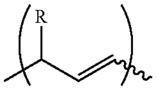

(IIb)

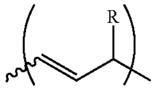

(IIc)

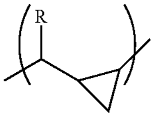

(IId)

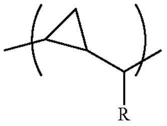

wherein R is methyl or hydrogen. The double bond in formula (IIa) and (IIb) may be cis or trans.

In embodiments in which X is (IIa) or (IIb) and the double bond is trans, R is preferably methyl. In embodiments in which the double bond is cis, R is preferably hydrogen.

The cyclopropyl group of fragment (IIc) or (IId), may be cis or trans.

In preferred embodiments in which X is (IIc) or (IId) R is preferably methyl.

In some especially preferred embodiments X is a fragment of formula (IIc) and the wax ester has the formula (IIe):

(IIe)

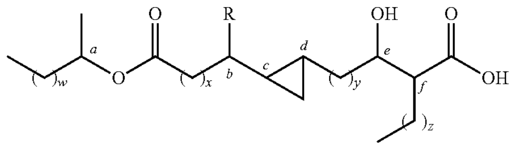

wherein w is from 2 to 40, x is from 2 to 40, y is from 2 to 40, z is from 4 to 40 and R is hydrogen or an alkyl group.

w is from 2 to 40, preferably from 6 to 36, more preferably from 10 to 32, for example from 12 to 28, and preferably from 14 to 24.

x is preferably from 2 to 40, preferably from 4 to 36, more preferably from 6 to 30, preferably from 8 to 24, for example from 10 to 20 and preferably from 12 to 18.

y is preferably from 2 to 40, preferably from 6 to 36, more preferably from 10 to 32, for example from 12 to 28, and preferably from 14 to 24.

z is preferably from 4 to 40, preferably from 8 to 36, more preferably from 12 to 32, for example from 16 to 30, more preferably from 20 to 28, for example from 22 to 26.

R may be hydrogen or an alkyl group. Preferably R is hydrogen or a $C_1$ to $C_4$ alkyl group. Preferably R is hydrogen or methyl. Most preferably R is methyl.

In the structure IIe, each of the chiral centres indicated at a, b, c, d, e and f may independently have either an (R) or an (S) configuration. Each cyclopropyl group may have either absolute stereochemistry and may have a trans or a cis configuration.

Any of the stereocentres indicated by a, b, c, d, e and f may be racemic.

Suitable salts of wax esters include ammonium, alkali metal and alkaline earth metal salts, for example salts of lithium, potassium, sodium, calcium or barium.

The wax ester compounds may be used as single compounds prepared synthetically and/or may be included in mixtures of synthetic compounds and/or may be included in mixtures isolated from natural sources. Any of these compounds could be used in the preparation of synthetic esters or be present in naturally occurring esters.

In some embodiments the antigen is provided as the free acid (i.e. a mycolic acid wax ester).

In some embodiments the antigen is an ester of a wax ester.

Suitable esters include esters of monohydric alcohols, polyhydric alcohols and sugars.

Ester antigens for use herein may be monoesters, diesters or polyesters of wax esters. Each ester may include one or more mycolic acid groups and one or more alcohol or sugar moieties. Antigens which are mixed esters including alcohols and sugars may also be used, for example compounds including an alcohol ester moiety and a sugar ester moiety.

Some preferred antigens for use in the present invention are sugar esters of a wax ester.

When a sugar ester is present this may be a monosaccharide, disaccharide or an oligosaccharide.

Suitable sugar units which may be included are those based on hexoses and those based on pentoses.

Suitable sugar esters for use herein are compounds of formula (III):

$$(W)_x\text{—}(S)_y\text{—}(W')_z \qquad \text{(III)}$$

wherein x is from 1 to 6, y is from 1 to 12, z is from 0 to 10, each W and each W is independently a mycolic acid wax ester residue including a 3-hydroxy acid moiety and each S is a monosaccharide unit.

In some embodiments x is from 1 to 4, preferably from 1 to 3, more preferably x is 1 or 2 and most preferably x is 1.

When x is greater than 1 and y is greater than 1, each M may be bonded to the same or different monosaccharide unit.

In some embodiments z is 0 to 6, preferably 0 to 4, more preferably 0 to 2, for example 0 or 1. In some embodiments preferably z is 1.

When z is greater than 1 and y is greater than 1, each M' may be bonded to the same or different monosaccharide unit.

Each W or W is a mycolic acid wax ester residue. By this we mean to refer to the portion of the wax ester molecule other than the acidic proton.

Each W and W may be the same or different. When x is greater than 1, each W may be the same or different. When z is greater than 1, each W may be the same or different.

The compounds of formula (III) are sugar esters of mycolic acid wax esters. Thus each acidic unit of the mycolic acid wax ester residues W and/or W' is bonded to an alcoholic group of a monosaccharide unit to form an ester linkage. Preferably each W and/or W' is bonded to a primary alcoholic group of a monosaccharide unit.

Suitable sugar ester compounds include monomycolates, dimycolates, trimycolates and tetramycolates; and mixed esters of sugar and alcohols.

In some embodiments y is between 1 and 6, preferably between 1 and 4, more preferably between 1 and 3. In some embodiments most preferably y is 1 or 2, especially 2.

In some embodiments the compound of formula (III) is an ester formed from one mycolic acid wax ester unit and one monosaccharide unit.

In some embodiments, the compound of formula (III) is an ester formed from one mycolic acid wax ester unit and two monosaccharide units wherein the two monosaccharide units are joined to form a disaccharide. Thus in such embodiments the compound of formula (III) is an ester formed from one mycolic acid wax ester unit and a disaccharide.

In some preferred embodiments, the compound of formula (III) is an ester formed from two mycolic acid wax ester units and two monosaccharides, that is two mycolic acid wax ester units and a disaccharide. In such cases, the compound has the formula W—S—S—W' in which each monosaccharide unit S may be the same or different.

In some preferred embodiments the ratio of mycolic acid units (W and W' combined total) to monosaccharide units(s) is approximately 1:1.

In some embodiments x+z=y.

Preferably the or each monosaccharide unit S has from 3 to 8 carbon atoms, preferably 5 or 6.

In some embodiments the or each monosaccharide unit has 6 carbon atoms. In preferred embodiments the or each monosaccharide unit S is an aldose.

Suitably each S is independently selected from allose, altrose, galactose, glucose, gulose, idose, mannose, talose, fructose, psicose, sorbose, and tagatose. Each S may be independently selected from allose, altrose, galactose, glucose, gulose, idose, mannose and talose. In some embodiments each S is independently selected from glucose and mannose. In some preferred embodiments each S is glucose.

Each monosaccharide unit may be present as the D or L isomer. Preferably each is present as the natural D isomer. Each monosaccharide unit may be present as the α form or the β form.

In some embodiments, y is 2 and the compound of formula (III) includes a disaccharide unit. In such a disaccharide unit, the monosaccharides may be connected in any suitable way. As the skilled person will appreciate, the nature of the bonding between the two monosaccharide units will determine the nature of the disaccharide.

Suitably the disaccharide is selected from sucrose, lactose, maltose, trehalose, cellobiose, kojibiose, nigerose, isomaltose, sophorose, laminaribiose, gentiobiose, turanose, maltulose, palatinose, gentiobiulose, mannobiose, melibiose, melibiulose, rutinose, rutinulose and xylobiose.

In some preferred embodiments the disaccharide unit is selected from sucrose, lactose, maltose, trehalose, and cellobiose. One especially preferred disaccharide unit is trehalose.

Some especially preferred sugar esters for use herein are glucose esters.

Other especially preferred sugar esters are trehalose esters. Suitable trehalose esters include trehalose monomycolates and trehalose dimycolates. Trehalose dimycolates have the structure shown in formula IV wherein WE represents the residue of a mycolic acid wax ester:

Formula IV

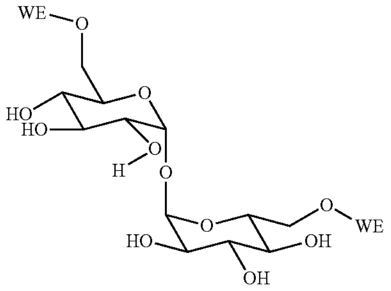

In formula IV each WE residue may be of the same or a different mycolic acid wax ester.

In some embodiments the or each monosaccharide unit S is a pentose.

In some embodiments each S is an aldopentose. Suitably each S is independently selected from arabinose, lyxose, ribose and xylose. In some preferred embodiments each S is arabinose.

Some preferred arabinose esters compounds of formula (III) for use as antigens in the present invention include arabinose monomycolates, arabinose dimycolates, triarabinose dimycolates and pentarabinose tetramycolates.

Some further preferred compounds for use as antigens in the present invention are mixed esters of sugars and alcohols, especially sugars and glycerol. Some especially preferred antigens include esters of wax esters and arabinose and glycerol and esters of wax esters trehalose/glucose and glycerol.

Other derivatives of mycolic acid wax esters that may be useful herein as antigens are the dicarboxylic acid compounds obtained by hydrolysis of the ester in the chain. Such compounds suitably have the formula:

(V)

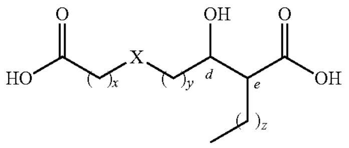

In some embodiments the antigen may be a compound of formula (S) $(W)_x$—$(S)_y$-$(M)_{z'}$, where W, S, x and y are as defined in relation to compound (III), M is a mycolic acid residue and z' is from 1 to 10. Preferably x is 1, z is 1 and y is from 1 to 3. Suitably Y is 1 or 2. Suitable mycolic acid residues M are as later described herein.

In some preferred embodiments the antigen is a synthetic antigen.

Suitably the antigen is at least 90% pure, for example at least 95% pure or at least 99% pure.

Preferably the antigen is a synthetic antigen which is at least 90%, preferably at least 95% or at least 99% pure.

By at least 90% pure we mean that at least 90% of the molecules of the antigen compound are identical i.e. the same homologue, the same stereoisomer and the same regioisomer.

In some embodiments a mixture of two or more antigens may be provided, for example at one or more positions on a substrate. In preferred embodiments in which mixtures are present the structure of all compounds and preferably the relative amounts of each compound are known.

Preferred mixtures are mixtures of synthetically prepared antigens.

An advantage of using synthetically prepared antigens is that the compounds may be provided in high purity. Natural mycolic acid wax esters contain complex mixtures of different homologues which are very difficult to separate. The use of synthetic compounds allows single compounds or known mixtures to be used. This enables antigens having a high degree of specificity and/or sensitivity for a particular antibody or antibodies to be used.

In some embodiments the system may comprise an adjuvant compound which enhances the binding of the biomarker with the antigen. For example, when the system comprises a substrate which carries the antigen, the substrate may carry an adjuvant compound which enhances the binding of the biomarker with the antigen.

In some embodiments the substrate may carry one or more further antigens, for example one or more further mycolic-acid derived antigens. For example, when the system comprises a substrate which carries the antigen, the substrate may carry one or more further mycolic-acid derived antigens.

Each of the one or more further antigens is suitably selected from one or more of the following classes of compounds:

(i) mycolic acids obtained from natural sources;
(ii) synthetically prepared mycolic acids;
(iii) salts of mycolic acids;
(iv) esters of mycolic acids (i) and/or (ii);
(v) sulfur-containing mycolic acids and/or salts or esters thereof;
(vi) simple structural analogues of mycolic acids and/or salts or esters thereof;
(vii) further mycolic acid wax esters or salts or derivatives thereof.

In some embodiments the system may comprise two or more different antigens, for example at different positions on a substrate. The two or more antigens may each be wax ester derived antigens.

Alternatively the system may comprise one or more wax ester derived antigens and one or more further antigens selected from among classes (i) to (vi).

Mycolic acids obtained from natural sources (i) are typically available as mixtures. These typically contain different classes of mycolic acids and each class will usually contain a complex mixture of different classes and different homologues.

It is highly advantageous to use synthetically prepared mycolic acids (ii) since these are available as single compounds in high purity (for example greater than 95% or greater than 99%). The use of single compounds allows greater selectivity to be achieved.

Salts of natural mycolic acids and/or synthetic mycolic acids (iii) may be useful. Suitable salts include ammonium, alkali metal and alkaline earth metal salts, for example salts of lithium, potassium, sodium, calcium or barium.

Suitable esters (iv) for use as further antigens include esters of simple monohydric and polyhydric alcohols and sugar esters. Suitable esters include glycerol esters of mycolic acids. Some particularly preferred antigens are sugar esters of mycolic acids. Some naturally occurring sugar esters of mycolic acids are trehalose monomycolates or trehalose dimycolates (also known as cord factors). Cord factors can be isolated as mixtures from natural sources. Esters of mycolic acids for use herein as antigens may be synthetically prepared. They may be prepared by esterification of synthetically prepared mycolic acids or by esterification of mycolic acids isolated from natural sources.

By sulfur-containing mycolic acids and/or esters or salts thereof (v) we mean to refer to synthetic compounds which are analogues of natural mycolic acid compounds rather than naturally occurring compounds that contain sulfur. Suitable sulfur-containing mycolic acid derivatives may include any compound in which one or more carbon atoms and/or one or more oxygen atoms of a mycolic acid derived compound has been replaced by a sulfur atom. Sulfur-containing mycolic acid derivatives also include compounds in which a hydrogen substituent has been replaced with a moiety "SX" wherein X is hydrogen, $SR^1$ or $COR^2$ in which $R^1$ is an optionally substituted alkyl, alkenyl, acyl or aryl group and $R^2$ is an optionally substituted alkyl, alkenyl or aryl group.

Simple structural analogues of mycolic acids and/or esters or salts thereof (vi) which may be used herein as antigens include compounds which include fewer functional groups and/or stereocentres than are found in natural mycolic acid compounds but have many structural features in common, for example they include a similar number of carbon atoms and have a simpler substitution pattern.

Synthetically prepared antigens are preferred as they can be prepared in high purity.

Suitable mycolic acid classes for use herein as further antigens include keto mycolic acids having the structure shown in formula IVa; hydroxy mycolic acids having the structure shown in formula IVb; alpha mycolic acids having the structure shown in formula IVc; and methoxy mycolic acids having the structure shown in formula IVd. Such mycolic acids may be included directly as the free acid or as an ester or salt thereof.

IVa

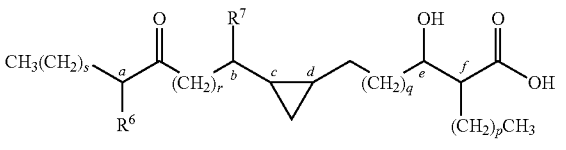

IVb

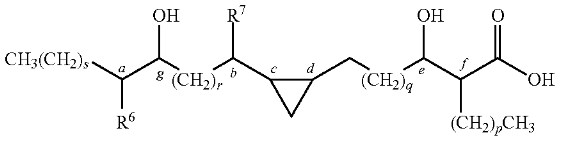

IVc

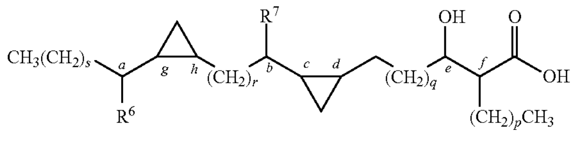

-continued

IVd

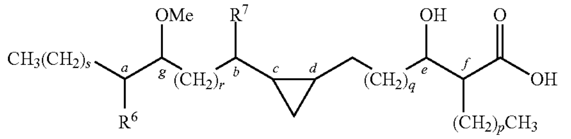

In each of the structures IVa, IVb, IVc and IVd $R^6$ may be hydrogen or $C_1$ to $C_4$ alkyl. Preferably $R^6$ is hydrogen or methyl.

In each of the structures IVa, IVb, IVc and IVd $R^7$ may be hydrogen or $C_1$ to $C_4$ alkyl. Preferably $R^7$ is hydrogen or methyl.

In each of the structures IVa, IVb, IVc and IVd p is preferably from 4 to 40, preferably from 8 to 36, more preferably from 12 to 32, for example from 16 to 30, more preferably from 20 to 28, for example from 22 to 26.

In the structures IVa, IVb, IVc and IVd q is preferably from 2 to 40, more preferably from 4 to 36, for example from 6 to 30, preferably from 8 to 24, for example from 10 to 20 and preferably from 12 to 18.

In the structures IVa, IVb, IVc and IVd, r is preferably from 2 to 40, for example from 6 to 36, preferably from 10 to 32, for example from 12 to 28, and preferably from 14 to 24.

In the structures IVa, IVb, IVc and IVd, s is preferably from 2 to 40, for example from 6 to 36, preferably from 10 to 32, for example from 12 to 28, and preferably from 14 to 24.

In the structures IVa, IVb, IVc and IVd, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IVa it is possible that the stereocentre designated a will be racemic as this is a readily epimerisable position.

In addition to the compounds illustrated by the structures IVa, IVb, IVc and IVd, other classes of mycolic acids may be useful as further antigens in the present invention. Suitable mycolic acid compounds may include an alkene functional group in place of the proximal cyclopropyl group. Further suitable classes of mycolic acids include those substituted with epoxy and alkene groups in the meromycolate moiety in place of the distal cyclopropyl, methoxy, hydroxy or keto groups. The proximal group in such compounds may be alkene or cyclopropyl. The structure of such compounds will be known to the person skilled in the art. Thus each further antigen used in the method of the present invention is preferably a mycolic acid-derived antigen selected from keto mycolic acids, hydroxy mycolic acids, alpha mycolic acids, methoxy mycolic acids, epoxy mycolic acids and alkene mycolic acids.

Each of the above-described mycolic acid compounds may be used as single compounds prepared synthetically and/or may be included in mixtures of synthetic compounds and/or may be included in mixtures isolated from natural sources. Any of these compounds could be used in the preparation of synthetic esters or be present in naturally occurring esters such as cord factors.

In some embodiments the antigen is an ester of a mycolic acid.

Suitable esters include esters of monohydric alcohols, polyhydric alcohols and sugars.

Ester antigens for use herein may be monoesters, diesters or polyesters. Each ester may include one or more mycolic acid groups and one or more alcohol or sugar moieties. Antigens which are mixed esters including alcohols and sugars may also be used, for example compounds including an alcohol ester moiety and a sugar ester moiety.

Some preferred antigens for use in the present invention are sugar esters of a mycolic acid.

When a sugar ester is present this may be a monosaccharide, disaccharide or an oligosaccharide.

Suitable sugar units which may be included are those based on hexoses and those based on pentoses.

Suitable sugar esters for use herein are compounds of formula (III):

$$(M)_x\text{-}(S)_y\text{-}(M')_z \quad \text{(III)}$$

wherein x is from 1 to 6, y is from 1 to 12, z is from 0 to 10, each M and each M' is independently a mycolic acid residue including a β-hydroxy acid moiety and each S is a monosaccharide unit.

When z is greater than 1 and y is greater than 1, each M' may be bonded to the same or different monosaccharide unit.

Each M or M' is a mycolic acid residue. By this we mean to refer to the portion of the acid molecule other than the acidic proton.

Each M and M' may be the same or different. When x is greater than 1, each M may be the same or different. When z is greater than 1, each M' may be the same or different.

The compounds of formula (III) are sugar esters of mycolic acid. Thus each acidic unit of the mycolic acid residues M and/or M' is bonded to an alcoholic group of a monosaccharide unit to form an ester linkage. Preferably each M and/or M' is bonded to a primary alcoholic group of a monosaccharide unit.

Suitable sugar ester compounds include monomycolates, dimycolates, trimycolates and tetramycolates; and mixed esters of sugar and alcohols.

Especially preferred sugar esters are esters of glucose, trehalose and arabinose. Trehalose monomycolates, trehalose dimycolates and arabinose esters are preferred.

Step (a) may involve providing a substrate which carries the antigen.

Any suitable substrate may be used. For example the substrate may be a multiwell plate, typically made of polystyrene of the type commonly used in ELISA assays. Multiwell plates of this type are known to the person skilled in the art. In such embodiments the antigens are suitably immobilised on the substrate by conventional means.

In some preferred embodiments the substrate is a porous substrate.

The porous substrate may be any material which allows another medium to pass through it. Suitably the porous substrate allows liquid compositions and semi-solid or viscous liquid compositions (for example gels and pastes) to pass through.

Any suitable porous substrate may be used. Suitably the porous substrate is a woven material. Preferably the porous substrate is a cellulosic material.

The porous material may carry the antigen. The antigen may be carried within the porous material or on the surface of the porous surface.

Preferably the antigen forms a chemical interaction with the surface of the substrate. This may involve a polar interaction, for example dipole-dipole interactions or hydrogen bonding; or a non-polar interaction, for example Van der Waals forces.

In some preferred embodiments the antigen forms hydrogen bonds with functional groups at the surface of the substrate.

To prepare the substrate the antigen may be directly applied to the substrate.

In some preferred embodiments in which the substrate is a cellulosic material a solution or suspension of the antigen may be applied to the substrate and the solvent allowed to evaporate. Without wishing to be bound by theory it is believed that hydrogen bonds form between the antigen and hydroxy groups of the cellulose.

Suitably the antigen is dissolved in a solvent. This may be an organic solvent, for example a mixture of hexanes; or an aqueous solvent, for example a buffer. The solution of antigen is suitably applied to the substrate and the solvent is then allowed to evaporate.

The antigen may be encapsulated, for example in a liposome.

Suitably a small spot of antigen is applied to the substrate at one or more positions.

Areas of the substrate which do not contain an antigen spot or spots may be "blocked", for example an impermeable coating may be applied to the surface of the substrate in these regions.

In step (b) of the method of the present invention, wherein the system comprises a substrate which carries the antigen, the substrate is contacted with a sample obtained from the individual. For the avoidance of doubt the sample is collected from the individual prior to carrying out the method of the present invention which is an in vitro method.

Any suitable sample may be tested using the present invention. Suitably the sample is selected from serum, blood, saliva, urine or sputum. In some embodiments the sample is blood. It may be serum.

The sample may contain a biomarker which becomes bound to or interacts with the antigen or antigens in the system.

The sample may be directly contacted with the system or it may be diluted, filtered or otherwise purified prior to contact with the system. Suitable diluents, filtration methods and purification techniques will be known to the person skilled in the art.

The sample is suitably contacted with the system as a liquid or semi-liquid composition. Preferably it is a liquid composition.

In some embodiments the sample is diluted before contacting with the system. It may be diluted with an aqueous composition, suitably an aqueous buffer. Preferably it is diluted with an aqueous buffer having a pH of 6 to 8, preferably about 7. A casein buffer is especially preferred.

In some embodiments, wherein the system comprises a substrate which carries the antigen, the substrate may be immersed in the sample or a composition comprising the sample.

In some embodiments, wherein the system comprises a substrate which carries the antigen, the sample or a composition comprising the sample may be passed over the surface of the substrate.

In some embodiments, wherein the system comprises a substrate which carries the antigen, in which the substrate is a porous substrate the sample or a composition comprising the sample is contacted with a surface of the substrate and allowed to pass through the substrate.

In such embodiments the substrate may suitably be a sheet material. The sample or a composition comprising the sample may pass from one edge of the substrate to the opposite edge or may be contacted with a face of the substrate and pass through the substrate to the opposite face.

The sample or a composition comprising the sample may be contacted with the entire area of the substrate or a portion of the substrate, suitably the portion which carries the antigen.

Step (c) of the method of the present invention involves detecting the presence or absence of the binding of a biomarker in the sample with the antigen.

Any suitable method may be used to detect the presence or absence of the binding of the biomarker.

In some preferred embodiments step (c) involves the steps:

(i) contacting the system with a composition comprising a secondary antibody; and (ii) observing the system.

In some preferred embodiments wherein the system comprises a substrate which carries the antigen, step (c) may involve the steps:

(i) contacting the substrate with a composition comprising a secondary antibody; and (ii) observing the substrate.

Suitably the composition comprising a secondary antibody comprises a carrier for the secondary antibody. The carrier is suitably a colorimetric substrate or is able to bind to a colorimetric substrate. The carrier for the secondary antibody may be selected from nanoparticles of a metal or nanoparticles of a polymeric material.

The composition comprising a secondary antibody may comprise a secondary antibody bound to an enzyme, for example an alkaline phosphatase. In such embodiments using a secondary antibody bound to an enzyme, a colorimetric substrate may then be used to enable binding of the antigen to an antibody in the sample to be detected/observed.

Step (c) may involve contacting the system, for example the substrate if present, with a composition comprising colloidal gold particles, wherein the colloidal gold particles carry a secondary antibody.

Any antibody or antibody conjugate which interacts with the biomarker may be used as the secondary antibody. Preferred secondary antibodies include Immunoglobulin G and Immunoglobulin M.

In some embodiments the secondary antibody is linked to an enzyme via bio conjugation. Such secondary antibodies are well known to the person skilled in the art and are commonly used in ELISA assays.

In some preferred embodiments step (c) involves contacting the substrate with a composition comprising colloidal gold particles wherein the colloidal gold particles carry a secondary antibody.

The composition comprising colloidal gold particles is preferably an aqueous suspension of gold nanoparticles.

Suitably the nanoparticles have an average size of from 1 to 200 nm, preferably from 5 to 150 nm, suitably from 10 to 100 nm, suitably from 20 to 80 nm, for example about 40 nm.

The composition may comprise one or more further ingredients for example cosolvents, preservatives, or buffering agents.

Preferably the composition comprises a buffer. Preferably the composition has a pH of from 5 to 9, preferably from 6 to 8, for example about 7. In some especially preferred embodiments the composition comprises a casein buffer.

Suitably the nanoparticles of gold carry a secondary antibody on their surface.

The antibody suitably forms an interaction with the surface of the gold nanoparticles.

In some preferred embodiments the gold nanoparticles are coated with a composition which promotes interaction with the secondary antibody. Preferably the gold particles are coated with a polymer. Suitable polymers are able to stabilize the gold particles and covalently bind antibodies.

Suitably there is one or more washing steps between step (c) (i) and step (c) (ii).

After the substrate is contacted with a composition comprising colloidal gold particles, the substrate is suitably washed. Preferably it is washed with a composition comprising a buffer.

Preferably it is washed with a composition of pH 6 to 8, suitably about 7. An aqueous composition comprising a casein buffer is especially preferred.

Step (ii) involves observing the substrate.

Suitably in embodiments in which the biomarker is present in the sample a colour change in the region of the substrate which carries the antigen is observed. If the biomarker is absent no colour change is observed.

Thus in preferred embodiments a positive sample in which a biomarker has bound with a particular antigen causes a colour change and a negative sample in which there is no binding causes no colour change.

In some embodiments step (ii) may involve quantitatively measuring the colour change. Quantitative analysis of this type may also help determine the severity of infection with a mycobacterial disease.

Step (ii) may also involve measuring a response change, for example a colour change over time. This information may also be useful in determining the type or extent of infection with a mycobacterial disease.

However in preferred embodiments step (ii) may involve simply visually observing the presence or absence of a colour change to provide a qualitative assessment.

In the method of the present invention when the sample is contacted with the substrate in step (b), if the biomarker is present it interacts with the antigen carried on the substrate and is thus "tethered" to the surface of the substrate.

If no biomarker is present no interaction occurs with the antigen and the biomarker is not present at the surface of the substrate.

In step (c) (i) the substrate may be contacted with the composition comprising colloidal gold particles which carry a secondary antibody or an enzyme-linked secondary antibody. If following step (b) the biomarker is carried on the surface of the substrate the secondary antibody interacts with the biomarker and tethers the gold particles to the substrate. If no biomarker is carried on the surface of the substrate then the secondary antibody and appendent gold particles or enzyme pass through the substrate.

The gold particles have a red colour. Thus when a biomarker is present the region of the substrate which carries the antigen is red at the end of step (c) (i). If no biomarker is present no such colouration of the substrate is observed.

When the secondary antibody is linked to an enzyme in the manner of an ELISA assay the method may suitably include a step of adding a composition comprising a colorimetric substrate. The colorimetric substrate suitably undergoes a colour change upon reaction with the enzyme indicating the presence of the enzyme and thus the secondary antibody and the biomarker. Suitable enzyme compositions are commonly used in ELISA assays and will be known to the person skilled in the art.

A particular advantage of the present invention is that it enables a very quick, simple test to be carried out to determine whether or not a particular sample contains a biomarker. Suitably it is used to determine whether or not the sample contains a biomarker indicative of exposure to mycobacteria, for example an antibody indicative of infection with or exposure to a mycobacterial disease. The method of the present invention may be carried out at remote locations, for example where there is no or limited access to hospitals, clinics, laboratories or specialist services. The colour change may provide an immediate or almost immediate indication of whether the provider of the sample is infected with a mycobacterial disease.

The method of the present invention may be carried out using traditional ELISA methodology. Such methods are well known to the person skilled in the art and commonly known variations are within the scope of the invention.

The present invention may thus provide the use of a mycolic acid wax ester derived antigen in an ELISA assay to determine whether an individual is infected with a mycobacterial disease. Preferred features of this use are as defined in relation to the method of the first aspect.

In some preferred embodiments the method of the first aspect of the present invention comprises the steps of:

(a) providing a porous substrate which carries a mycolic acid wax ester derived antigen;
(b) contacting the substrate with the sample; and
(c) (i) contacting the substrate with a composition comprising colloidal gold particles wherein the colloidal gold particles carry a secondary antibody; and
(ii) observing the substrate.

Preferred features of this preferred method are as previously defined herein.

Suitably the porous substrate is a cellulosic substrate. Suitably the composition comprising colloidal gold particles is an aqueous suspension of gold nanoparticles.

In especially preferred embodiments of the present invention the system comprises at least two different mycolic-acid derived antigens, suitably at different positions on a substrate. At least one of the mycolic acid derived antigens is a mycolic acid wax ester derived antigen. The other antigens may be selected from any of the types of compounds previously described herein. Suitably the different antigens are each located at different positions on a substrate.

The diagnosis of mycobacterial diseases, for example Johne's disease, is known to be very difficult.

The present inventors have found that when the system comprises two or more different antigens, considering the observations related to these antigens in combination can lead to a higher accuracy in diagnosis of a disease. Thus the method may allow the interaction with multiple antigens to be measured simultaneously. In such embodiments step (c) involves detecting the presence or absence of the binding of a biomarker with each antigen separately.

By measuring the interaction with more than one antigen the present invention allows a greater degree of sensitivity and specificity to be achieved.

The inventors have surprisingly found that using a combination of different mycolic acid derived antigens which comprises a mycolic acid wax ester derived antigen allows a much more accurate and reliable diagnosis. These results can also be achieved quickly and cheaply.

Suitably in the method of the present invention the presence or absence of a colour change at two or more different positions on a substrate in combination leads to the determination of whether or not an individual is infected with a mycobacterial disease, especially Johne's disease.

In preferred embodiments the one or more further antigens are selected from wax esters, free mycolic acids, sugar esters of mycolic acids and sugar esters of wax esters.

In some embodiments the system comprises more than two mycolic-acid derived antigens, suitably at different positions on a substrate. It may suitably comprise at least 3 different mycolic acid derived antigens, for example at least 4, at least 5 or at least 6, suitably at different positions on a substrate.

In some especially preferred embodiments the system comprises from 5 to 8 different antigens. Preferably each of these antigens is synthetically prepared. Preferably each is at least 90% pure, preferably at least 95% pure, for example at least 99% pure. The use of a combination of a number of different antigens allows a higher degree of sensitivity and specificity to be achieved and enables distinction between different mycobacterial diseases.

According to a second aspect of the present invention there is provided a kit for determining the presence or absence of a biomarker in a sample, the kit comprising:

(x) a system which comprises a mycolic acid wax ester derived antigen; and
(y) a composition comprising a secondary antibody.

Suitably the second aspect of the present invention provides a kit for determining the presence or absence of a biomarker in a sample, the kit comprising:

(x) a substrate which carries a mycolic acid wax ester derived antigen; and
(y) a composition comprising a secondary antibody.

Preferred features of the second aspect are as defined in relation to the first aspect and features described in relation to the second aspect may also apply to the first aspect. As described above the substrate may be a multiwell plate as commonly used in an ELISA assay and the composition comprising a secondary antibody may comprise an enzyme linked secondary antibody. In such embodiments the kit may further comprise a composition comprising a substrate for the enzyme. As will be understood by the skilled person the substrate for the enzyme is a small molecule with which the enzyme reacts and is distinct from the substrate previously defined herein which is a carrier for the antigens. The substrate for the enzyme may be a colorimetric substrate.

As previously described herein, in some preferred embodiments the substrate is a porous material, preferably a porous sheet material, for example a cellulosic material. In such embodiments the composition comprising the secondary antibody may be a composition comprising particles of colloidal gold wherein the colloidal gold particles carry the secondary antibody on their surface.

In the kit of the second aspect the substrate is preferably located within a suitable housing.

Preferably the substrate is positioned within the housing so as to enable the sample to contact the substrate.

Suitably the housing includes an aperture to enable the sample to contact the substrate in the region which carries the antigen.

In some preferred embodiments in which the substrate is porous it is positioned within the housing to enable the sample to pass through from one side of the substrate to the other.

The housing may further comprise a chamber to collect the sample and other compositions after they pass through the substrate. The chamber may include an absorbent material to soak up the excess sample, excess secondary antibody composition and/or any washing compositions.

The housing may be made from any suitable material. Preferably it is a plastic housing.

The absorbent material is preferably a sponge-like material.

According to a third aspect of the present invention there is provided a device comprising a housing and a system; wherein the system comprises an antigen which is a mycolic acid wax ester derived antigen or an analogue thereof.

Suitably this third aspect of the present invention provides a device comprising a housing and a substrate; wherein the substrate carries the mycolic acid wax ester derived antigen.

Preferred features of the device of the third aspect are as defined in relation to the first and second aspects. The kit of the second aspect preferably comprises a device of the third aspect and a composition comprising a secondary antibody.

When used to analyse known samples of sera from cattle some of whom had been infected with Johne's disease, the method of the present invention was found to provide a faster and more accurate method of discrimination between positive and negative samples compared with using standard methods of the prior art. The method of the present invention is also more suitable for point of care use than prior art methods, for example in environments with limited access to laboratories.

Embodiments of the invention which use a porous substrate and a secondary antibody carried on colloidal gold particles are particularly suitable for use in remote locations.

When the present invention is used to test for disease antibodies indicative of infection with a mycobacterial disease, for example Johne's disease, it can provide results very quickly, with good accuracy and at relatively low cost. It therefore provides significant advantages over the prior art.

Furthermore it was surprisingly noted that the free acid mycolic acid wax esters and the hydrolysis product diacids (see formula (V)) were able to discriminate between positive and negative samples, since the use of free mycolic acid compounds in ELISA assays has provided poor results.

Whilst wax-esters of mycolic acids and their sugar esters have been previously extracted from natural sources they have not previously been prepared synthetically.

Compounds obtained from natural sources usually contain a mixture of compounds for example a mixture of isomers or a mixture of homologues. The natural sources contain many different compounds and these are difficult to separate.

Synthetic preparation of the antigens is very beneficial as it allows single compounds to be prepared in a high degree of purity.

A fourth aspect of the present invention provides a composition comprising at least 90 wt % of a single compound of formula (I) or an ester of a salt thereof:

(I)

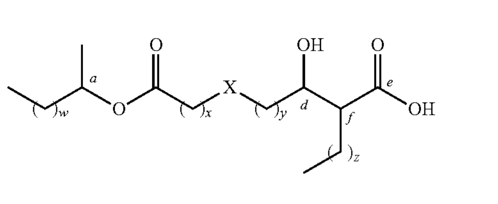

wherein w is from 2 to 40, x is from 2 to 40, y is from 2 to 40, z is from 4 to 40 and X is a three carbon fragment including an alkane, alkene or cyclopropyl moiety.

The compound of formula (I) is as defined in relation to the first aspect.

The composition of the fourth aspect comprises at least 90 wt % of a single compound of formula (I). Suitably the single compound is a single homologue, single stereoisomer and single regioisomer. Suitably the composition of the fourth aspect comprises at least 95 wt % of a single compound, preferably at least 97 wt %, more preferably at least 99 wt %.

The provision of highly purified single compounds is advantageous as the different compounds interact with different antibodies and thus elicit different immune responses. As such these single compounds can be used in therapeutic applications. They can also be used as adjuvants in vaccination.

Suitably the invention provides a composition of the fourth aspect for use in treatment of a disease of the immune system.

The present invention may thus provide compositions for the treatment of diseases of the immune system, in particular the immune system of mammals and especially humans.

Suitably the disease treated is a disease involving an out of control immune response or pathology causing immune response, for example an allergic immune disease or an autoimmune disease.

Preferably the compounds of the present invention are useful in the treatment of a disease in which Th2-lymphocyte activity contributes to the immune disease.

Examples of diseases which may be treated according to the present invention include asthma, rhinitis, hay fever, eczema and other allergic diseases; and autoimmune diseases, for example, systemic lupus erythematosus, Goodpasture's syndrome, Grave's disease, Myasthenia Gravis, type I diabetes and multiple sclerosis.

In preferred embodiments, the present invention is useful in the treatment of asthma and other allergic diseases. Allergic diseases are known to the person skilled in the art and include, but are not limited to, allergic asthma, allergic rhinitis, allergic conjunctivitis, eczema, airway hyperactivity, eosinophilic airway inflammation and atopic dermititis.

Suitably the invention may provide a composition of the fourth aspect for use as an adjuvant in vaccination.

The invention may further comprise a vaccine composition comprising a composition of the fourth aspect and a further antigen.

It is believed that particular compounds of formula I may be selected to control the immune response achieved in vaccination. For example some compounds may be particularly effective adjuvants for use in vaccination against extracellular antigens, for example viruses and extracellular bacteria. Such compounds may then preferentially elicit Th17 and Th1 lymphocyte responses and immune defences supported by these T-cell subsets. Other compounds may be particularly effective adjuvants for use in vaccination against intracellular antigens, for example mycobacteria, listeria and cancer. Such compounds may then preferentially elicit Th1 and cytotoxic T-lymphocyte responses and immune defences supported by these T-cell subsets.

In some alternative embodiments the compound of formula I may be selected such that when used as an adjuvant a humoral immune response is elicited that is supported by Th2 lymphocytes and provides protection against among other parasitic infections.

In especially preferred embodiments the composition of the fourth aspect comprises at least 90 wt % of a single compound having the formula A, B, C, D, E, F or G:

A

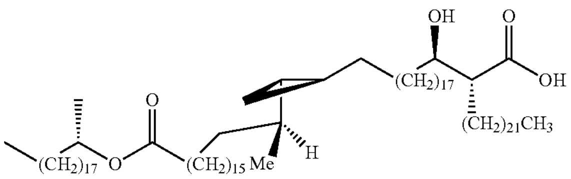

B

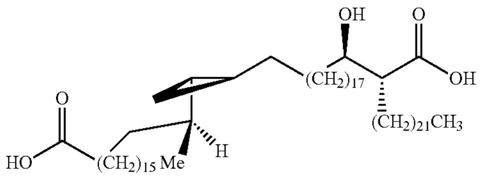

C

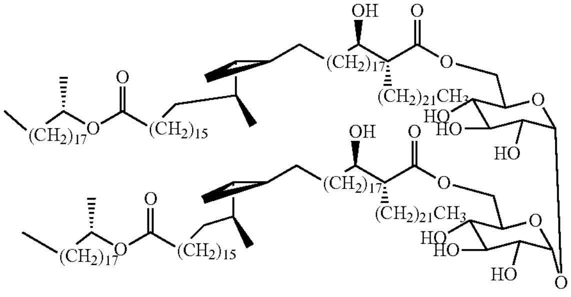

D

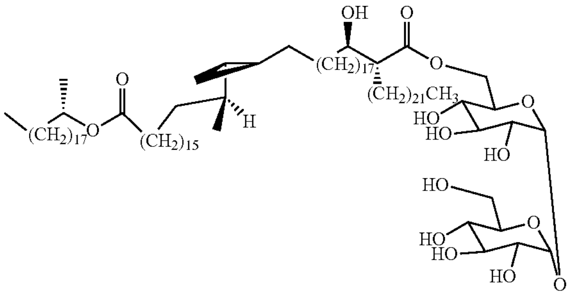

E

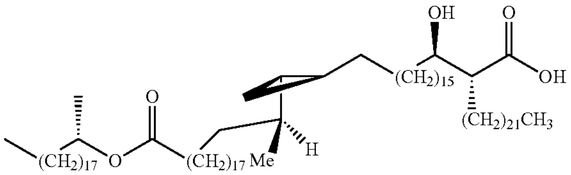

F

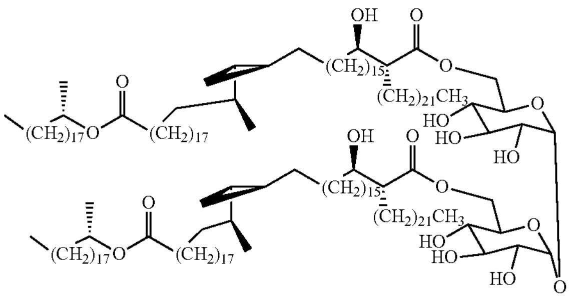

-continued

G

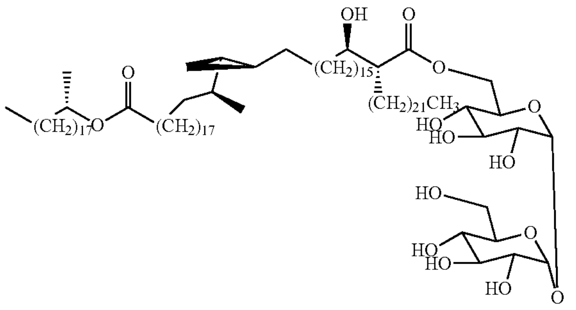

The invention will now be further described with reference to the following non-limiting examples:

EXAMPLE 1: SYNTHESIS OF WAX ESTER 33

Compound 21 was prepared by the method described in "The synthesis of single enantiomers of meromycolic acids from mycobacterial wax esters", Juma'a R. Al Dulayymi, Mark S. Baird, Evan Roberts and David E. Minnikin, Tetrahedron, 2006, 62, 11867-11880.

21

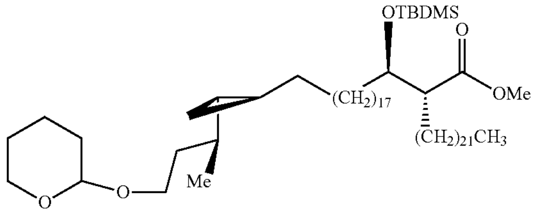

The wax ester 33 was prepared using the following reactions shown in scheme 1. The selection of suitable conditions such as reaction time and temperature are within the competence of the person skilled with the art.

Scheme 1

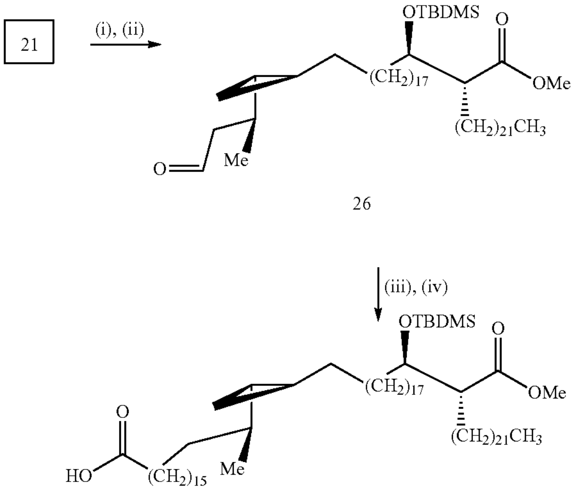

26

27

(i) pyridinium-p-toluene sulfonate (PTSA), MeOH, 84%, (ii) PCC, dichloromethane 93%; (iii) lithium bis(trimethylsilyl)amide, 25, dry THF, (80%); (iv) dipotassium azodicarboxylate, THF, methanol, $CH_3COOH$ (80%).

In order to generate the full wax ester, the ω-dicarboxylic acid mono-ester 27 needed to be coupled to (S)-2-eicosanol 31.

The ω-dicarboxylic acid mono-ester 27 was esterified with S-2-eicosanol 31 through a Steglisch esterfication reaction (Scheme 2):

Scheme 2

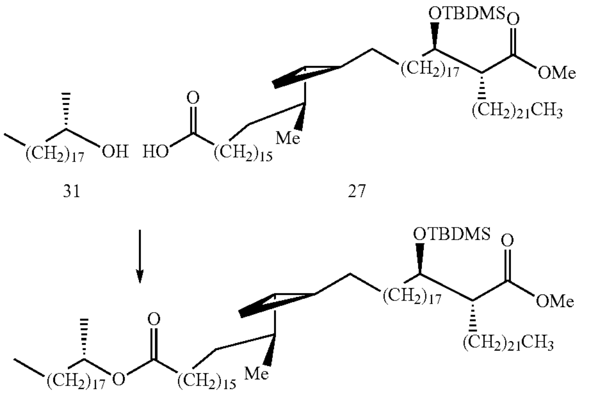

31 27

32

(i) DCC, DMAP, dry dichloromethane (80%)

Removal of the silyl ether and methyl ester protection was achieved in two steps to produce the free wax ester mycolic acid 33 (Scheme 3):

Scheme 3

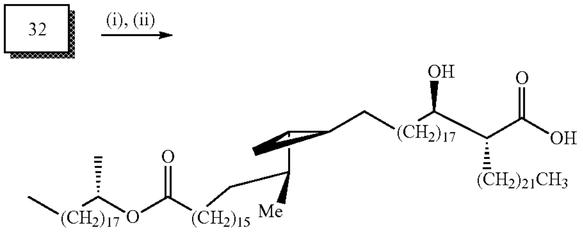

33

(i) hydrogen fluoride-pyridine complex, dry THF (71%); (ii) tetrabutylammonium hydroxide solution 5% aq. solution (60%).

The ω-dicarboxylic acid 34 has been previously isolated from cells as a component of a complex mixture. The compound 34 was also synthesized starting from the ω-dicarboxylic acid mono-ester 27 after TBDMS deprotection and hydrolysis. (Scheme 4):

Scheme 4

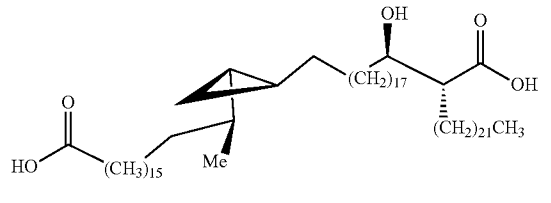

34

(i) HF-Pyridine, dry THF, 17 hrs (85%), (ii) LiOH, THF, water-MeOH, 17 hrs (85%).

EXAMPLE 2: SYNTHESIS OF TREHALOSE MONOMYCOLATE AND TREHALOSE DIMYCOLATE OF WAX ESTER 33

The protected wax ester mycolic 35 was prepared from the corresponding free hydroxy wax ester 33 by reaction with an excess of tert-butyldimethylsilyl chloride and imidazole in the presence of 4-dimethylaminopyridine for 24 h at 70° C., followed by hydrolysis of the TBDMS ester on the acid group by stirring in THF for 15 minutes in the presence of (4%) of aqueous solution of tetrabutyl ammonium hydroxide.

The compound 35 was coupled to hexatrimethylsilyl trehalose 36 using 1-(3-dimethylaminopropyl-3-ethylcarbodiimide hydrochloride, 4-dimethylaminopyridine and 4 Å molecular sieves in dichloromethane for six days at ambient temperature. This gave the protected TDM (trehalose dimycolate) 37 (52%) and the protected TMM (trehalose monomycolate) 38 (32%). Both of the compounds 37 and 38 were deprotected in two steps, including sugar deprotection to give 39 and 40 and finally TBDMS deprotection to give the free TDM 41 and the free TMM 42 (Scheme 5).

Scheme 5

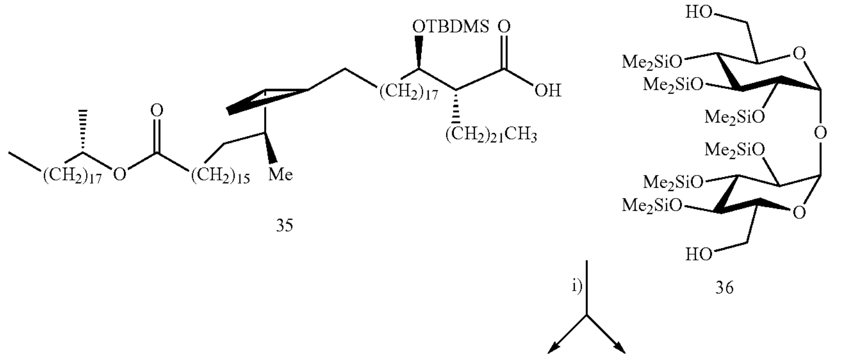

35 36

-continued
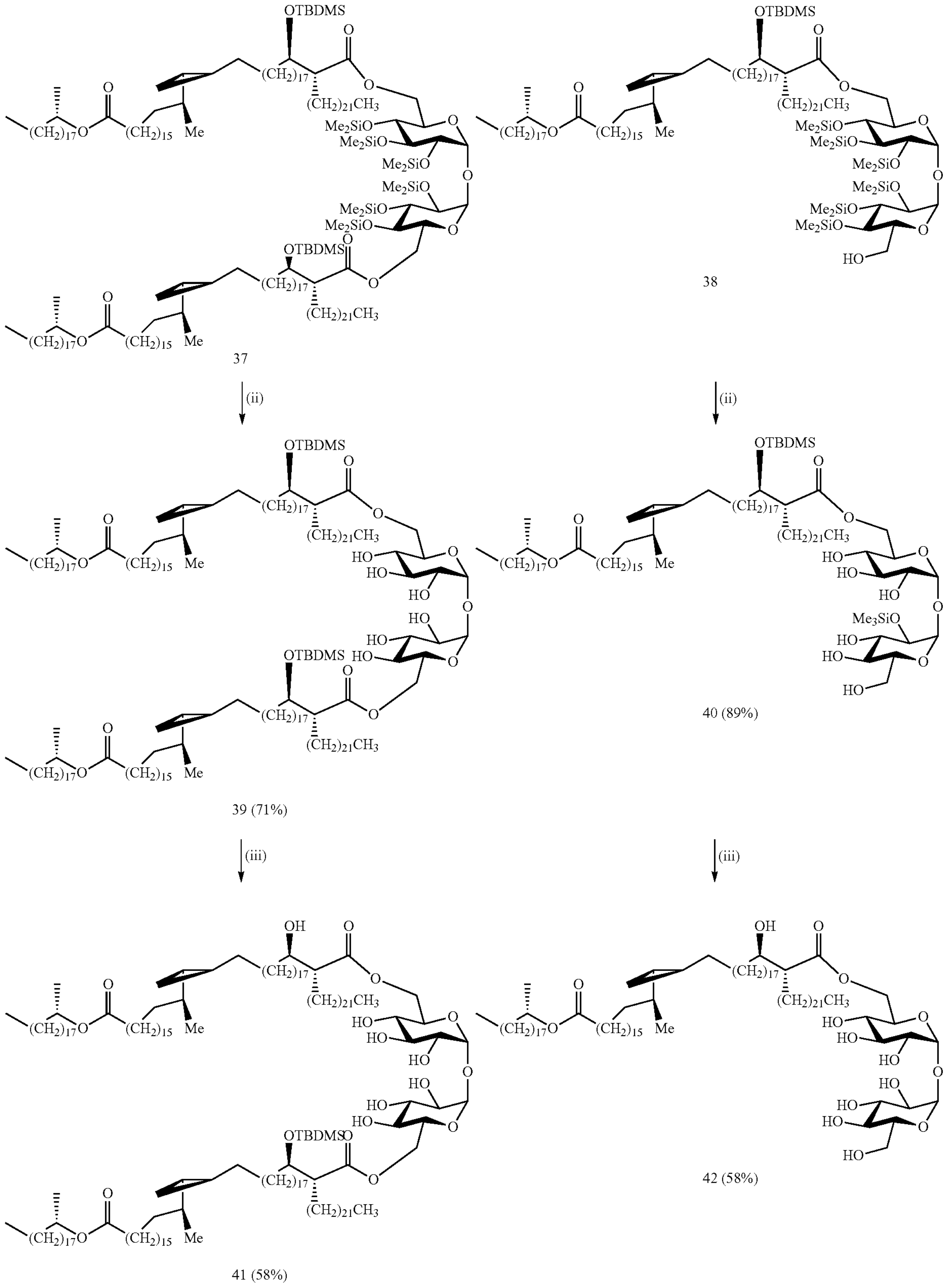
(i) EDCI, DMAP, dry DCM, 6 days; (ii) tetra-n-butyl ammonium fluoride, dry THF; (iii) hydrogen fluoride-pyridine complex, dry THF

EXAMPLE 3

The following additional wax esters were synthesised by the above or analogous methods:

A

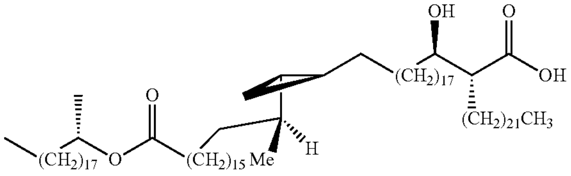

B

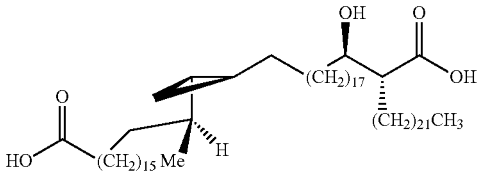

C

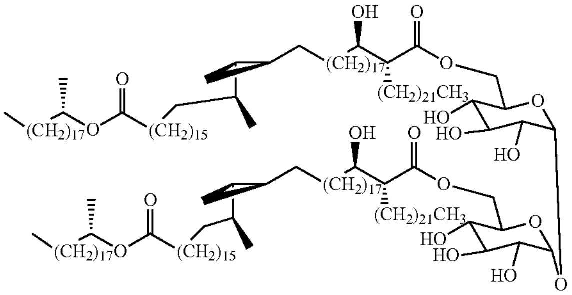

D

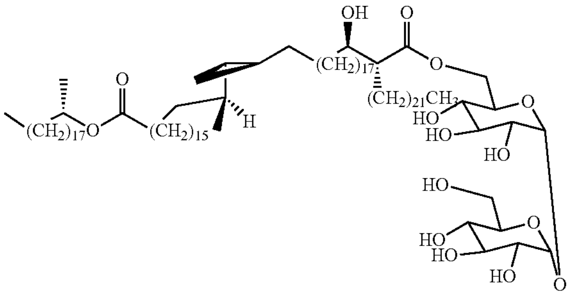

E

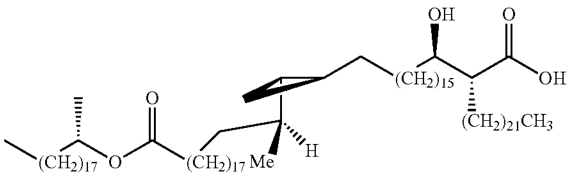

-continued

F

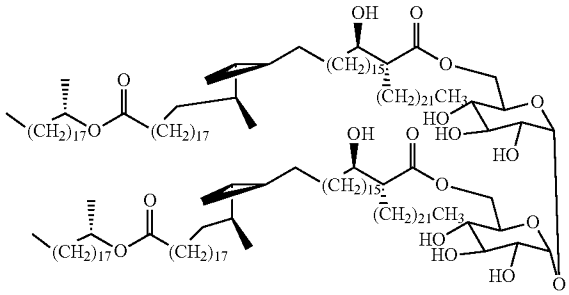

G

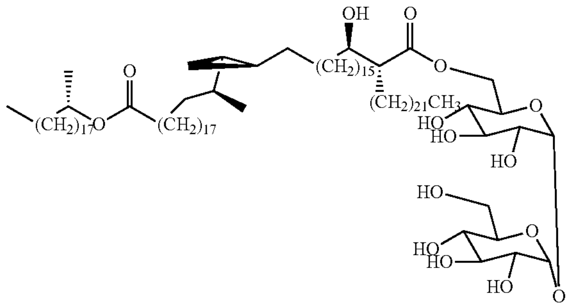

EXAMPLE 4

The binding of antibodies in serum of cattle infected with *M. tuberculosis* or *M. avium* with the antigens detailed in example 3 was measured in an ELISA assay.

ELISA assays were carried out as known to those practiced in the art using 96 well plates. In the first procedure, the ELISA assay was carried out on 96-well microplates and the purified antigens were dissolved in n-hexane at a concentration of 62.5 μg/ml. The antigen solutions were diluted and 50 μl and placed in each well. The plates were left to dry at room temperature overnight. Blocking was done with 0.5% casein/PBS (400 μl/well) and the plates are left to incubate at 25° C. for 1 h. The casein was aspirated using the LT-3500 plate washer and the plates flicked dry. Then the serum (1:20 dilution in 0.5% casein/PBS, pH 7.4) was added to the plate (50 μl/well) and left to incubate at 25° C. for 1 h. The serum was aspirated and washed three times with (casein/PBS, 400 μl/well) using the same plate washer and the plates were flicked dry again. After that, the secondary antibody, in the example given IgG Fc (1:1000 dilution in 0.5% casein/PBS) was added to the plate (50 μl/well) and the plates were left to incubate at 25° C. for 30 min. The plates were washed three times again with (casein/PBS, 400 μl/well) and dried. Then, the OPD substrate was added to the plates, which were left to incubate at 25° C. for 30 min. Finally, 2.5 M $H_2SO_4$ (50 μl/well) was added and the absorbances of each well were read at 492, 450 and 630 nm using an LT-4000 plate reader.

Serum used in this work was obtained from cattle infected with MAP, diagnosed as naturally infected with bovine TB, or known not to be infected using standard assays.

All measurements were taken as four replicates unless otherwise stated. These were averaged to provide the data in the table which are optical density measurements at 492 nm.

The results are given in Table 1 below:

TABLE 1

ELISA assays to detect antibodies in serum of cattle infected with bovine *M. tuberculosis* (B tb) or *M. avium paratuberculosis* (MAP). Shaded boxes represent absorbances above a cut-off set for positive response for the particular antigen. The first two samples are infected with *M. avium paratuberculosis* (MAP). Antigen B shows the ability to identify MAP infection and gives no signal with B tb infected serum. Other wax esters identify the MAP infected serum, but also give selective responses with some of the B tb+ samples and with B tb− samples, either due to co-infection with MAP or infection with other mycobacteria.

| | | Antigens | | | | | | |
|---|---|---|---|---|---|---|---|---|
| | | A | B | C | D | E | F | G |
| MAP (experimentally infected) | | 3.70 | 0.76 | 3.07 | 3.29 | 2.97 | 1.44 | 4.38 |
| MAP (Naturally infected) | | 4.38 | 0.72 | 4.06 | 4.00 | 3.88 | 4.00 | 4.38 |
| VLA (Naturally infected) bovis | 1 | 1.49 | 0.17 | 2.74 | 3.12 | 0.38 | 1.07 | 3.68 |
| | 2 | 2.59 | 0.15 | 1.81 | 3.20 | 0.54 | 0.67 | 2.78 |
| | 3 | 1.85 | 0.13 | 2.94 | 3.08 | 1.24 | 2.47 | 4.06 |
| | 4 | 2.51 | 0.16 | 2.15 | 1.69 | 1.82 | 0.67 | 0.63 |
| | 5 | 0.68 | 0.20 | 0.61 | 3.05 | 1.56 | 0.29 | 1.04 |
| | 6 | 1.70 | 0.21 | 0.26 | 1.43 | 2.03 | 0.18 | 0.88 |
| | 7 | 1.20 | 0.16 | 0.61 | 3.07 | 2.77 | 0.51 | 2.34 |
| | 8 | 3.02 | 0.21 | 1.86 | 1.51 | 3.29 | 2.23 | 1.39 |
| | 9 | 0.91 | 0.14 | 0.20 | 0.73 | 2.62 | 0.18 | 0.40 |
| | 10 | 0.57 | 0.19 | 0.22 | 0.82 | 1.02 | 0.24 | 0.52 |
| | 11 | 0.52 | 0.19 | 0.36 | 1.64 | 0.98 | 0.31 | 1.63 |
| | 12 | 3.94 | 0.27 | 0.64 | 0.95 | 4.05 | 1.08 | 1.54 |
| | 13 | 0.14 | 0.05 | 0.37 | 0.28 | 0.17 | 0.66 | 0.26 |
| | 14 | 0.19 | 0.05 | 0.99 | 0.40 | 0.13 | 0.23 | 0.22 |
| | 15 | 1.85 | 0.06 | 0.29 | 0.31 | 0.98 | 0.12 | 0.15 |
| | 16 | 1.30 | 0.07 | 0.12 | 0.18 | 1.25 | 0.62 | 0.15 |
| | 17 | 3.05 | 0.10 | 1.80 | 0.78 | 1.20 | 0.47 | 0.11 |
| | 18 | 0.87 | 0.08 | 0.70 | 0.19 | 0.39 | 0.52 | 0.27 |
| | 19 | 0.69 | 0.07 | 0.68 | 0.28 | 1.45 | 0.69 | 0.11 |
| | 20 | 0.59 | 0.10 | 0.36 | 0.18 | 0.73 | 1.08 | 1.54 |
| VLA (Non-vaccinates | 21 | 1.34 | 0.12 | 0.24 | 0.47 | 0.33 | 0.25 | 0.37 |
| | 22 | 0.47 | 0.10 | 0.51 | 0.27 | 0.21 | 0.25 | 0.14 |
| | 23 | 0.65 | 0.11 | 0.14 | 0.45 | 0.47 | 0.17 | 0.24 |
| | 24 | 0.47 | 0.10 | 0.34 | 1.17 | 0.32 | 0.21 | 0.51 |
| | 25 | 0.60 | 0.12 | 0.18 | 0.50 | 0.87 | 0.15 | 0.27 |
| | 26 | 0.43 | 0.12 | 4.03 | 1.13 | 1.03 | 3.66 | 0.82 |
| | 27 | 0.50 | 0.15 | 3.79 | 1.18 | 0.62 | 1.96 | 0.55 |
| | 28 | 0.79 | 0.17 | 0.71 | 0.91 | 0.96 | 0.36 | 0.46 |
| | 29 | 0.33 | 0.16 | 0.64 | 2.86 | 0.45 | 0.29 | 1.58 |
| | 30 | 0.76 | 0.19 | 0.26 | 0.30 | 0.74 | 0.26 | 0.16 |
| | 31 | 0.35 | 0.22 | 0.70 | 1.58 | 0.67 | 0.45 | 1.99 |
| | 32 | 0.14 | 0.06 | 0.21 | 0.11 | 0.16 | 0.06 | 0.06 |
| | 33 | 0.14 | 0.05 | 0.07 | 0.08 | 0.14 | 0.08 | 0.10 |
| | 34 | 0.14 | 0.05 | 0.08 | 0.08 | 0.15 | 0.11 | 0.07 |
| | 35 | 0.14 | 0.06 | 0.22 | 0.11 | 0.20 | 0.31 | 0.07 |
| | 36 | 0.13 | 0.06 | 0.50 | 0.10 | 0.16 | 0.12 | 0.07 |
| Cut-off for conditional formating | | 0.85 | 0.30 | 0.85 | 0.85 | 0.85 | 0.85 | 0.85 |
| Cut-off for sensitivity and specificity | | >.85 | >0.30 | >.85 | >.85 | >.85 | >.85 | >.85 |

In Table 1, "VLA" means Veterinary Laboratories Agency, the source of the samples.

The invention claimed is:

1. A method of determining whether an individual is infected with a mycobacterial disease, the method comprising:

(a) providing a system which comprises an antigen;

(b) contacting the system with a sample obtained from the individual; and (c) detecting the presence or absence of binding of a biomarker for the mycobacterial disease in the sample with the antigen;

wherein the antigen is a mycolic acid wax ester derived antigen of formula (I) or an ester or salt thereof:

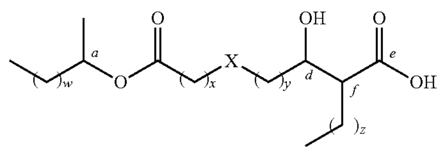

(I)

wherein w is from 2 to 40, x is from 2 to 40, y is from 2 to 40, z is from 4 to 40, and X is a three-carbon fragment including an alkane, alkene, or cyclopropyl moiety.

2. A method according to claim 1 wherein steps (a), (b) and (c) are carried out in the order (a) followed by (b) followed by (c).

3. A method according to claim 1 wherein the antigen is present on a substrate in the system and/or in one or more solutions or suspensions in the system; and/or encapsulated in the system, for example in liposomes.

4. A method according to claim 1 which involves:

(a) providing a substrate which carries the mycolic acid wax ester derived antigen;

(b) contacting the substrate with a sample obtained from the individual;

(c) detecting the presence or absence of binding of a biomarker for the mycobacterial disease in the sample with the mycolic acid wax ester derived antigen.

5. A method according to claim 1 wherein the biomarker is an antibody.

6. A method according to claim 1 wherein the biomarker is a disease antibody indicative of the presence of *Mycobacterium avium* paratuberculosis.

7. A method according to claim 1 wherein the individual is a ruminant.

8. A method according to claim 4 wherein the substrate carries one or more further antigens selected from one or more of the following classes of compounds:

(i) mycolic acids obtained from natural sources;

(ii) synthetically prepared mycolic acids;

(iii) salts of mycolic acids;

(iv) esters of mycolic acids (i) and/or (ii);

(v) sulfur-containing mycolic acids and/or salts or esters thereof;

(vi) simple structural analogues of mycolic acids and/or salts or esters thereof;

(vii) further mycolic acid wax esters or salts thereof.

9. A method according to claim 5 wherein step (c) involves the steps:

(i) contacting the system with a composition comprising a secondary antibody that interacts with the antibody in the sample; and (ii) detecting the presence or absence of binding of the antibody in the sample with the secondary antibody.

10. A method according to claim 5 wherein step (c) involves contacting the system with a composition comprising colloidal gold particles wherein the colloidal gold particles carry a secondary antibody that interacts with the antibody in the sample.

11. A kit for determining the presence or absence of a biomarker for a mycobacterial disease in a sample, the kit comprising:

(x) a system which comprises a mycolic acid wax ester derived antigen; and (y) a composition comprising a secondary antibody that interacts with the biomarker, wherein the mycolic acid wax ester derived antigen is a compound of formula (I) or an ester or salt thereof:

(I)

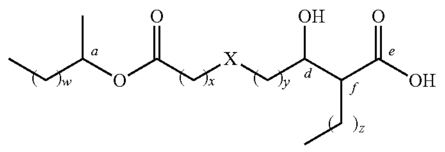

wherein w is from 2 to 40, x is from 2 to 40, y is from 2 to 40, z is from 4 to 40, and X is a three-carbon fragment including an alkane, alkene, or cyclopropyl moiety.

12. A composition comprising at least 90 wt % of a single compound of formula (I) or an ester or a salt thereof:

(I)

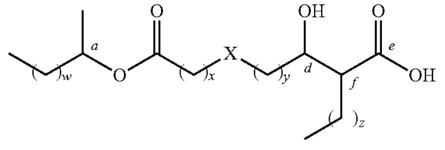

wherein w is from 2 to 40, x is from 2 to 40, y is from 2 to 40, z is from 4 to 40 and X is a three carbon fragment including an alkane, alkene or cyclopropyl moiety, which composition comprises at least 90 wt % of a single compound having the formula A, B, C, D, E, F or G:

A

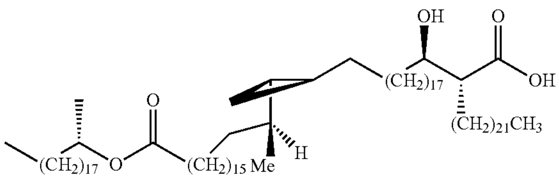

B

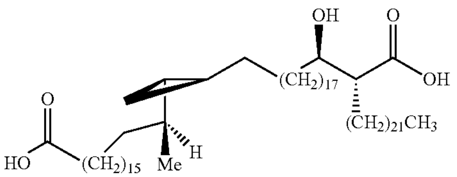

C

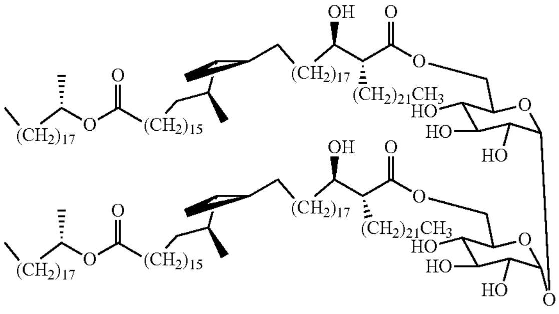

-continued

D

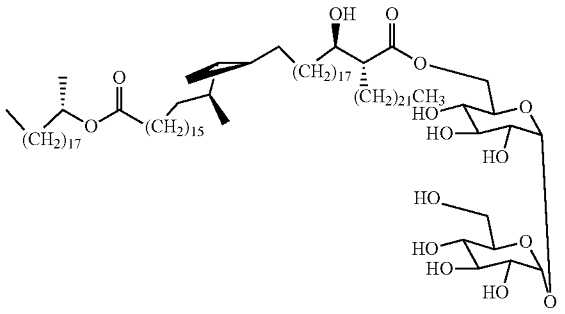

E

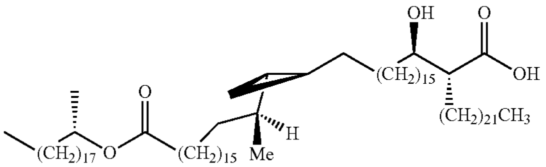

F

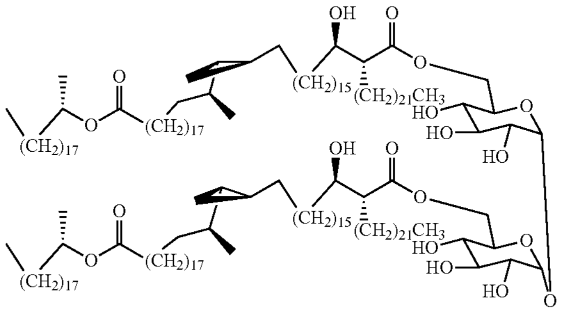

G

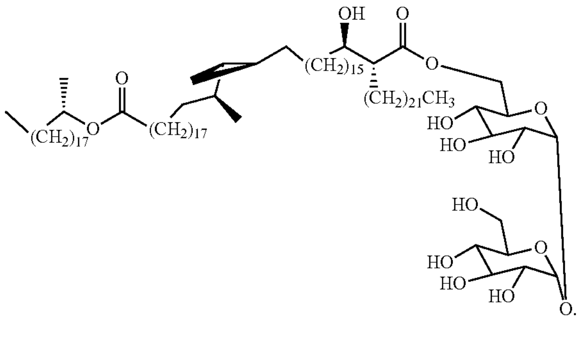

* * * * *